United States Patent [19]

Inokuchi et al.

[11] Patent Number: 5,006,111
[45] Date of Patent: Apr. 9, 1991

[54] MEDICAL PUMP DEVICE AND A METHOD FOR COMPENSATING A DEVIATION OF A MEASURED BLOOD FLOW RATE

[75] Inventors: Kiyoshi Inokuchi; Kenichiro Okadome; Yoichi Muto, all of Fukuoka; Yoshio Kawai, Musashino; Tadashi Onuma, Inashiki; Toshiharu Shirakami, Tokyo, all of Japan

[73] Assignee: Kureha Kagaku Kogyo Kabushiki Kaisha, Tokyo, Japan

[21] Appl. No.: 220,990

[22] Filed: Jul. 18, 1988

Related U.S. Application Data

[63] Continuation of Ser. No. 2,709, Nov. 24, 1986, abandoned.

[30] Foreign Application Priority Data

Apr. 5, 1985 [JP] Japan ................... 60-71997

[51] Int. Cl.$^5$ ............................. A61M 5/14
[52] U.S. Cl. ........................ 604/67; 600/17
[58] Field of Search ................ 128/DIG. 13; 600/16-18; 604/31, 50, 65-67; 623/3

[56] References Cited

U.S. PATENT DOCUMENTS

| | | | |
|---|---|---|---|
| 3,592,183 | 7/1971 | Watkins et al. | 604/67 |
| 3,885,251 | 5/1975 | Redroso | 128/1 D X |
| 3,911,897 | 10/1975 | Leachman | 128/10 |
| 4,135,253 | 1/1979 | Reich et al. | 128/1 D X |
| 4,154,227 | 5/1979 | Krause et al. | 128/1 D |
| 4,231,354 | 11/1980 | Kurtz et al. | 604/66 |
| 4,250,872 | 2/1981 | Tamari | 128/1 D |
| 4,432,468 | 2/1984 | Siff et al. | 604/65 |
| 4,546,759 | 10/1985 | Solar | 128/1 D |
| 4,588,404 | 5/1986 | Lapeyne | 128/1 D X |
| 4,598,697 | 7/1986 | Numazawa et al. | 128/1 D |
| 4,662,355 | 5/1987 | Pieronne et al. | 128/1 D |
| 4,782,817 | 11/1986 | Singh et al. | 600/17 |

FOREIGN PATENT DOCUMENTS 0075606  4/1983  European Pat. Off. .
2342078  9/1977  France .

Primary Examiner—William E. Kamm
Attorney, Agent, or Firm—Oblon, Spivak, McClelland, Maier & Neustadt

[57] ABSTRACT

A medical pump device is constructed so that a pulsation force is applied to the blood in the vicinity of an artery, which is reconstructed after a bypassing operation has been completed, so as to compensate for a deviation of an actual wave form of a blood flow in the vicinity of the reconstructed artery from a normal wave form thereof. The medical pump device is capable of minimizing the possibility of occurrence of a late obturation in an artery which is reconstructed after a reconstruction operation has been completed, and improving a rate of keeping open the reconstructed artery.

16 Claims, 13 Drawing Sheets

MEDICAL PUMP DEVICE AND A METHOD FOR COMPENSATING A DEVIATION OF A MEASURED BLOOD FLOW RATE

This application is a continuation of application Ser. No. 002,709, filed on Nov. 24, 1986, now abandoned.

BACKGROUND OF THE INVENTION

1. Field of the Invention

This intention relates to a medical pump device constituted so as to provide a pulsating blood flow superimposed on a spontaneous blood flow and, more specifically, it relates to a novel medical pump device effective to the improvement for the prognosis of the artery reconstructed by bypassing operation against the occlusion of a peripheral artery such as a limb artery. This invention further relates to a method for compensating a deviation of a measured blood flow rate in an artery from a referenced blood flow rate to thereby bring the measured blood flow rate near to the referenced blood flow rate.

2. Discussion of Background

In recent years, arterial obliteration (obliterans) has come into a problem as one of adult diseases with the increase in arteriosclerosis due to various causes. As the therapeutical method for the arterial obliteration, a so-called bypassing operation that recovers the blood flow by bypassing the portion of the occluded blood vessel with a patient's vein or an artificial blood vessel made of polytetrafluoroethylene or the like became popular along with the development and popularization of blood vessel surgery.

The bypassing technology provides satisfactory results for the abdominal aorta and ilium artery.

However, the reliability for the bypassing operation is not always sufficient for the thigh artery and those arteries on the peripheral side from the thigh artery, in the cases of early obliteration that the reconstructed artery is occluded as early as within about 48 hours after the surgical operation, or cases of later obliteration that the reconstructed artery is occluded within about 6 months to 3 years after the surgical operation.

By the way, a relationship between the cases of causing the early occlusion and the cases liable to cause the later occlusion and the blood flow rate waveform (change of the blood flow rate with time) after the surgical operation in the vicinity of the reconstructed artery has been shown recently.

That is, it has been made clear that among five blood flow waveforms O, I, II, III and IV shown in FIGS. 1(a), (b), (c), (d) and (e) (in each of the graphs, the abscissa corresponds to the time t and the ordinate corresponds to the blood flow rate S measured by utilizing the Doppler effect or electromagnetic flow-meter etc.), the waveforms III and IV shown in FIGS. 1(d), (e) have a concern with the cases causing early occlusion, while the waveform II shown in FIG. 1(c) has a concern with the cases causing prognostic occlusion and the waveforms O, I shown in FIGS. 1(a), (b) correspond to the cases causing relatively less prognostic occlusion.

Accordingly, the early occlusion, which is known to be caused by the presence of the occlusion at the sutured site or of the unexpected pathogenic occlusion, can be coped with by instantly searching the cause for the pathogenic change and applying repairement or reconstruction if the blood flow after the operation near the reconstructed artery takes the waveform of III or IV.

However, in the case of the later occlusion for which it has been statistically confirmed that about one-half of the cases showing the blood flow waveform of type II shown, for example, in FIG. 1(c) correspond to the later occlusion but the cause for which has not yet been clarified, no appropriate preventive measures have been established.

SUMMARY OF THE INVENTION

The present inventors have continued an earnest study for the improved prognosis of the reconstructed artery after the bypassing operation in order to solve the foregoing problems and, as a result, have accomplished this invention on the findings that the rate of keeping open the reconstructed artery after the operation can remarkably be increased by forcedly adding a pulsating movement for a predetermined period so that the blood flow waveform is substantially in a normal blood flow waveform (type O in FIG. 1(a)) even in a case where the spontaneous blood flow waveform just after the reconstructing operation near the reconstructed artery shows an abnormal waveform liable to cause the later occlusion.

This invention has been made based on the above finding and the object thereof is to provide a medical pump device capable of suppressing the risk that the later occlusion is resulted to the reconstructed artery after the reconstructing operation and of increasing the rate of keeping open the reconstructed artery.

The foregoing object can be attained in accordance with this invention by a medical pump device adapted such that a pulsating blood flow is added near the reconstructed artery so as to compensate the deviation of the blood flow waveform near the reconstructed artery after the bypassing operation from the normal blood flow waveform.

In the case where the medical pump device according to this invention is applied for a period, for example, about from two weeks to one month, to the vicinity of the reconstructed artery from which an abnormal blood flow waveform has been detected just after the reconstructing operation, the rate of keeping open the reconstructed artery can be increased in accordance with the finding as described above.

BRIEF DESCRIPTION OF THE DRAWINGS

This invention will be explained more specifically referring to the accompanying drawings.

In the accompanying drawings.

DETAILED DESCRIPTION OF THE PREFERRED EMBODIMENTS

Figure 2:
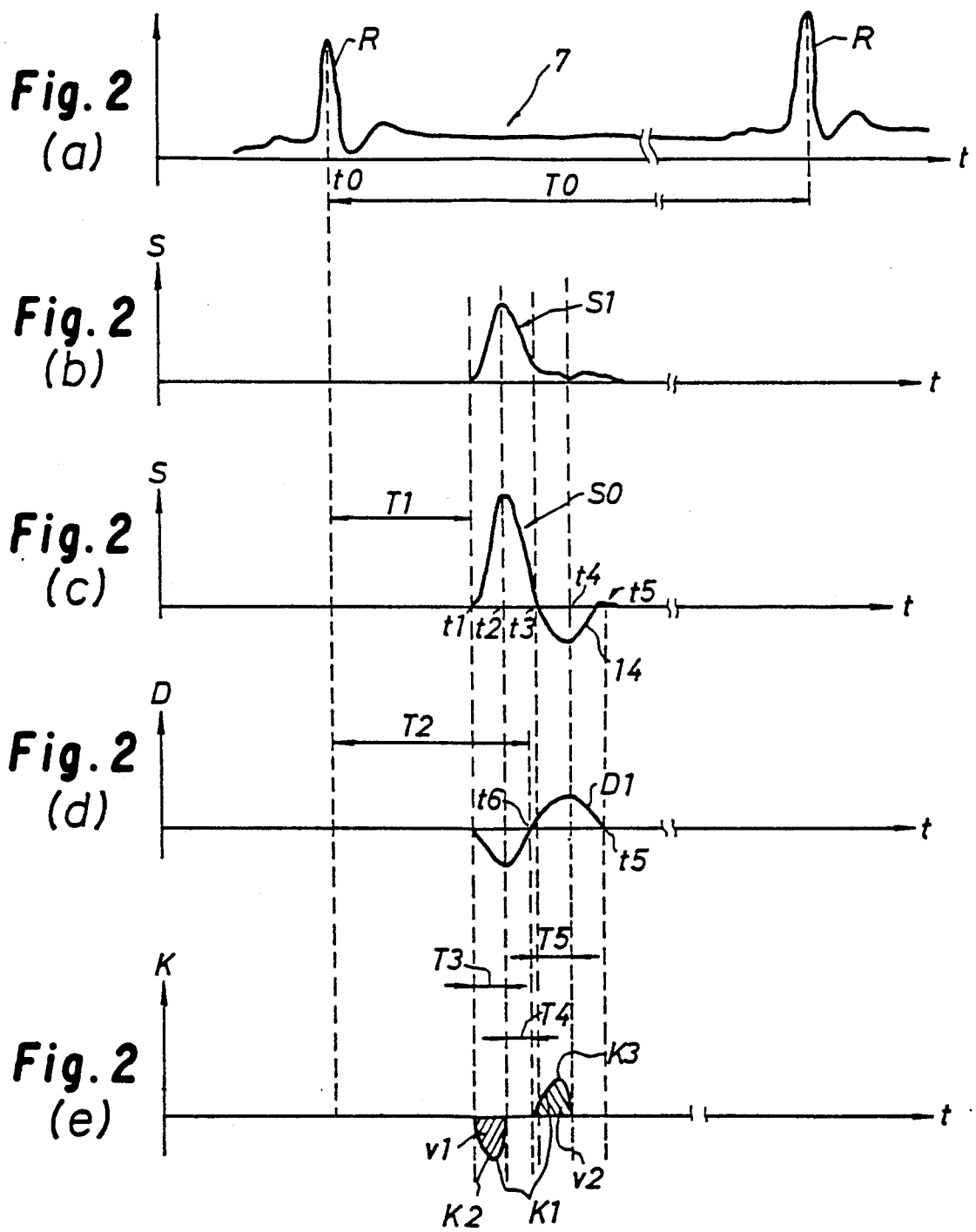
FIGS. 2(a) to 2(e) are time charts representing the output of an electrocardiograph, a blood flow rate pattern which may possibly cause the later occlusion, a pattern for the normal blood flow rate, a pattern for the difference in the flow rate, as well as one example of a pulsating flow pattern.

A medical pump device of a preferred embodiment according to this invention will then be explained referring to FIGS. 2(a) to (2(e) and 3.

Figure 3:
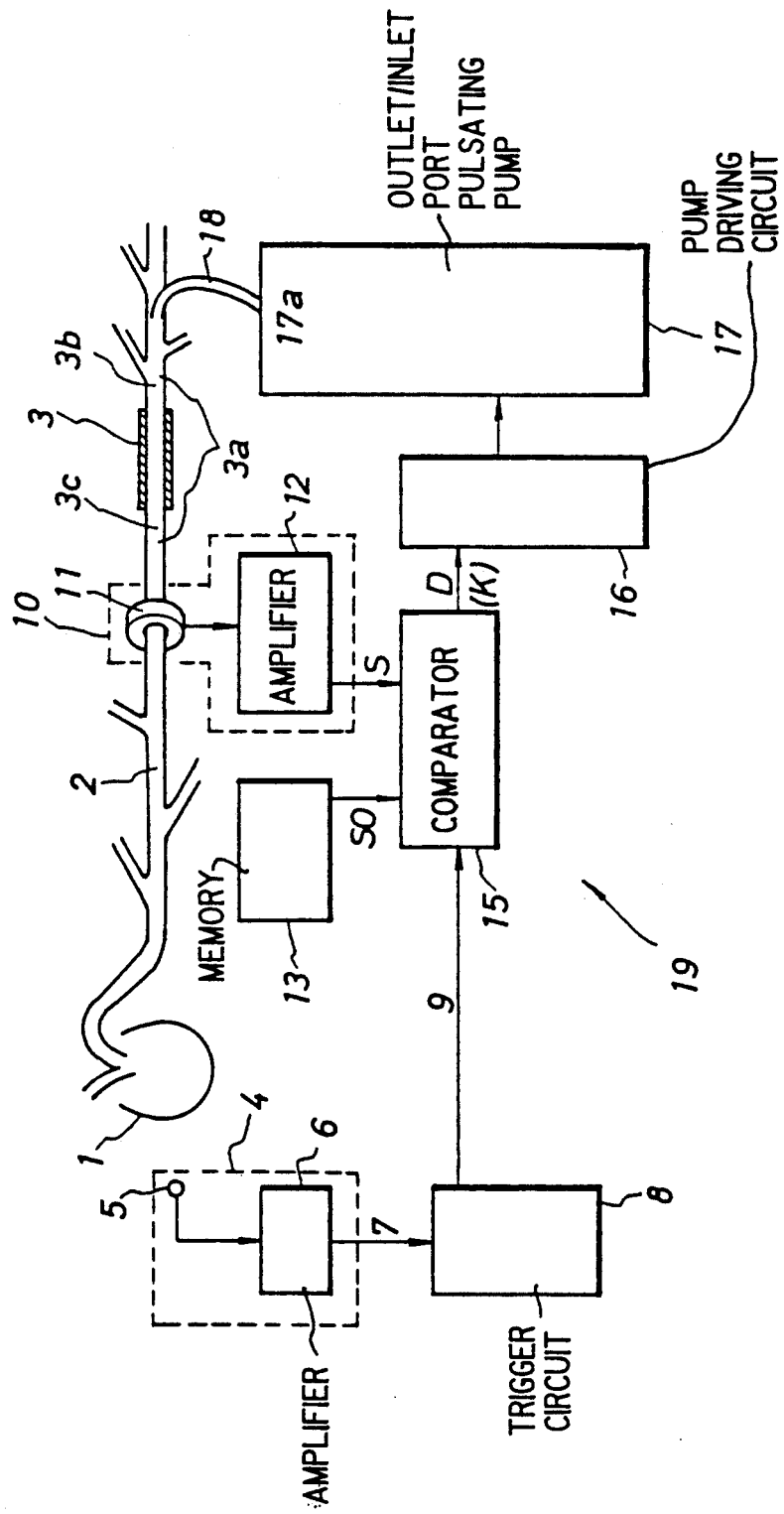
FIG. 3 is an explanatory view for the medical pump device in a preferred embodiment according to this invention.

In FIG. 3, there are a heart 1, an artery 2 and a reconstructed artery 3. 4 is an electrocardiograph comprising a detector 5 and an amplifier 6, in which a waveform signal 7 including the R waves and corresponding to the heart beat is issued as shown in FIG. 2(a). The duration $T_0$ between the two R waves is dependent on the kind of animal, metabolism (state of movement), etc. If an acoustic signal, pressure signal, electrical signal, etc. can be detected and outputted as a signal synchronized with the heart beat, a phonocardiograph or the like may be used instead of the electrocardiograph 4. Further, a blood flowmeter for detecting the change in the blood flow synchronized with the heart beat in the arterial portion upstream to the reconstructed artery 3 may be used instead of the electrocardiograph 4.

8 is a trigger circuit that receives the signal 7 from the electrocardiograph 4 and generates a driving signal 9 at each peak point $t_0$, $t_0+T_0$,—of the R wave corresponding to the contraction of the cardiac ventricular muscle and the delivery of the blood by way of the artery 2 to each portion of a body.

10 is a blood flowmeter, which comprises a detector 11 for detecting the blood flow waveform or blood flow rate S in the artery in the vicinity $3a$ of the reconstructed artery 3 at the upstream $3c$ or downstream $3b$ of the reconstructed artery 3 and an amplifier 12 that amplifies and issues a signal detected in the detector 11. The blood flowmeter 10 may be of any principle and type, so long as it can recognize the dynamic situation of the blood flow in the vicinity $3a$ of the reconstructed artery 3: for example, those utilizing the ultrasonic Doppler effect or electromagnetic flowmeter, etc. will do.

Figure 1:
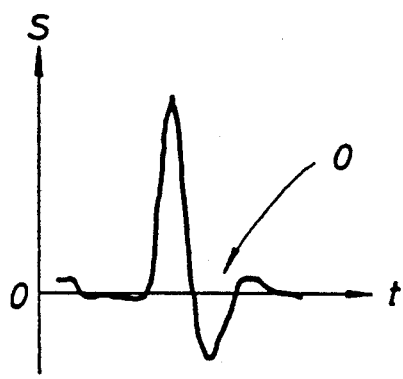
FIGS. 1(a) to 1(e) are graphs to explain the blood flow rate pattern which may possibly occur near the reconstructed artery after the reconstructing operation.
Figure 1:
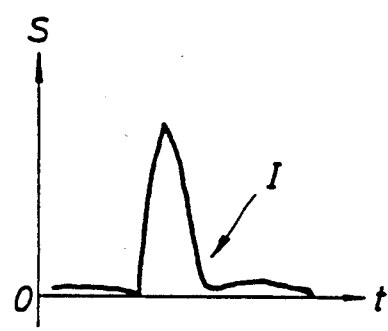
Figure 1:
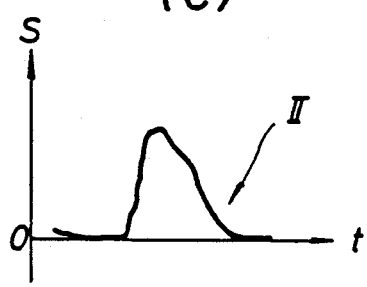
Figure 1:
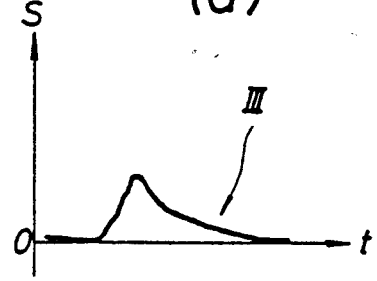
Figure 1:
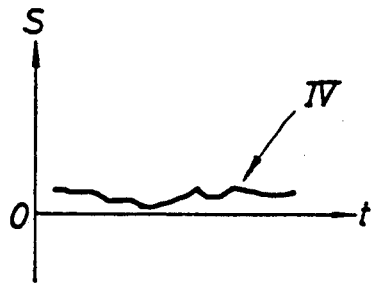

When the reconstructed artery 3 is desirably reconstructed (or the reconstructed artery 3 is normal), the form of the signal S to be outputted from the blood flowmeter 10 is $S_0$ as shown in FIG. 2(c) (similar to that in FIG. 1(a)). The normal signal $S_0$ has such a shape as rising from the time $t_1$ (= $t_0+T_1$) delayed by the time $T_1$, from the time $t_0$, which is determined by the distance of the reconstructed artery portion 3 from the heart 1 and by the pulse rate (number) of the heart 1, increasing during the period ($t_2-t_1$) corresponding to the contracting and relaxing movement of the heart 1, reaching the peak at the time $t_2$, decreasing during the period ($t_3-t_2$) to fall to zero at the time $t_3$, causing and increasing the backward flow during the period ($t_4-t_3$), reaching the negative peak at the time $t_4$ and then gradually decreasing thereafter to zero about at the time $t_5$.

Such a normal blood flow waveform signal $S_0$ as shown in FIG. 2(c) is stored in a memory 13.

In a case if the condition after the reconstructing operation is not quite satisfactory but there may be a possibility of causing the later occlusion (There is a case of causing the occlusion in the waveform of the type II, even if operation is satisfactory.), the shape of the blood flow waveform signal S outputted from the blood flowmeter 10 in the vicinity $3a$ of the reconstructed artery 3 is as shown by the reference $S_1$ in FIG. 2(b) (typically, the same as the type II shown in FIG. 1(c) but, depending on the case, those similar to the type I or III shown in FIGS. 1(b) or (d), for which the judgement is difficult).

The signal $S_1$ is substantially identical with the signal $S_0$ for the rising time $t_1$ and the peak reaching point $t_2$, but different from the normal blood flow waveform signal $S_0$ in that it has no backflowing region 14 between the time $t_3$ and the time $t_5$ and that the flow rate in the forward direction between the time $t_1$ and the time $t_6$ (substantially identical with time $t_3$) is smaller than that in the normal case.

15 is a comparator, which determines the difference: $D = S - S_0$ between the detected signal S from the blood flowmeter 10 and the reference signal $S_0$ from the memory 13, after the elapse of a predetermined delay time $T_1$ from the driving signal 9 and while the signal S is supplied from the blood flow meter 10. It generates a signal as shown by the reference $D_1$ (= $S_1 - S_0$) in FIG. 2(d) as the difference signal D, for example, in the case where the signal S from the blood flowmeter 10 is an abnormal blood flow waveform signal $S_1$.

16 is a pump driving circuit, 17 is a pulsating pump having a single outlet/inlet port $17a$ for the liquid and 18 is a catheter for connecting the single outlet/inlet port $17a$ of the pump 17 with the vicinity region $3a$ of the reconstructed artery 3, in which the pump driving circuit 16 drives the pump 17 based on the difference signal D so as to compensate the difference D, that is, reduce the difference D to thereby add a pulsating movement to the vicinity region $3a$ of the reconstructed artery 3 by way of the catheter 18. Saline water incorporated with a blood coagulation inhibitor is filled inside of the catheter 18 and the pump 17. As the pump 17, one having a high response speed, less leakage and less flow rate change is preferred.

As shown in FIG. 3, if the catheter 18 is connected to the downstream side $3b$ of the reconstructed artery 3, suction is applied through the catheter 18, for example, during the time period $t_1-t_6$ where $D<0$, while discharging is applied through the catheter 18 during the period $t_6-t_5$ where $D>0$. While on the other hand, if the catheter 18 is connected to the upstream side $3c$ of the reconstructed artery 3, discharge is applied during the time period $t_1-t_6$, while suction is applied during the time period $t_6-t_5$, for instance.

The treatment by the pump device 19 as has been described above is not necessarily applied permanently for a patient: it is usually sufficient to perform for about from two weeks to one month after the operation.

In the pump device 19, the comparator 15 may be a microprocessor or the like for the ease of computer-control. Further, the operation or manipulation parameters may be set manually while monitoring the blood flow waveform to thereby compensate the deviation from the normal blood flow waveform without using a comparator.

In the case of using the comparator 15, various kinds of parameters as described later may be inputted by way of a key board, write pen or the like, the values for the operation parameters may be indicated on real time, or the flow rate pattern, that is, the blood flow waveform may be detected by means of a blood flowmeter 10 sometimes (for example, each time the pulse number changes) to automatically compensate the operation parameters.

In the foregoing, if the pulsating movement is not given by the pump 17, since the blood flow waveform $S_1$ detected by the blood flowmeter 10 does not substantially change with time, it is not always necessary to dispose the blood flowmeter 10, the normal waveform memory 13 and the comparator 15. Once after the blood flow waveform $S_1$ has been detected and the difference signal waveform $D_1$ has been determined in the vicinity 3a of a particular reconstructed artery 3 after the operation, it is sufficient to maintain the difference signal waveform $D_1$ in the difference signal generator 15a and generate the difference signal D from the difference signal generator 15a synchronized with the driving signal 9 (with a time delay $T_1$).

Further, it is not always necessary for the comparator 15 to give a pattern identical with the difference D. That is, taking into consideration with elasticity of the artery portion 3a near the reconstructed artery 3, the response delay characteristics of the pump 17 or the like, the driving circuit 16 may also be supplied with a signal K for performing discharge (suction) and suction (discharge) at two directional flow volumes approximating to those defined by $D_1$ during the period $t_1-t_2$ (the period in which $D_1$ increases in the negative direction) and the period between the time $t_6$ (or $t_3$) $-t_4$ (the period in which $D_1$ increases in the positive direction), respectively, for example, as shown in FIG. 2(e). In this case, there is no practical problem even if the change of $K_1$ with time is different from the change of $D_1$ with time. The amounts of discharging (sucking) and of sucking (discharging) through the catheter 18 may be different from each other and, in the case of equalizing the amounts, the pulsating patterns may be different from $D_1$ or $K_2$, $+K_3$ as shown in FIG. 2(e), for instance, if the volume $V_1$ defined by $K_2$ is equalized to the volume $V_2$ defined by $K_3$ as shown in FIG. 2(e). Suction (discharge) may be performed by a liquid volume corresponding to the volume $V_1$ during the time period $t_1$ and discharge (suction) may be performed by liquid volume corresponding to the volume $V_1$ during the time period $t_3-t_5$ or $t_3$ to the next heart beating time.

In the comparator 15 providing predetermined times $t_1$, $t_2$, $t_3$, $t_4$, that is, the time period $T_1=t_1-t_0$, time period $t_3=t_2-t_1$ time period $T_4=t_3-t_2$, and time period $T_5=t_4-t_3$ relative to the time $t_0$ and the volume V1, V2, it is desirable that the time periods $T_1$, $T_3$, $T_4$ and $T_5$ and the volume $V_1$, $V_2$ can be set, that are made variable. These operation or manipulation parameters $T_1$, $T_3$, $T_4$, $T_5$, $V_1$, $V_2$ may be determined in comparison with the normal blood flow waveform $S_0$ as a reference in the case of detecting the abnormal blood flow waveform $S_1$ upon observing the blood flow waveform after reconstructing operation, and may be set initially to the comparator 15.

The adjusting range for the parameters $T_1$, $T_3$, $T_4$, $T_5$, $V_1$, $V_2$ are, for example, as described below.

Upon measurement for a mongrel adult dog with the standard heart beat number of about 120 cycles/min at a blood flow measuring portion apart by about 40 cm from the heart, $T_1=t_1-t_0\simeq140$ msec, $T_3=t_2-t_1\simeq50$ msec, $T_4=t_3-t_2\simeq40$ msec, and $T_5=t_4-t_3\simeq60$ msec. In the case of increasing the number of heart beat by the injection of drugs for the adult dog to about 160 cycles/min, $T_1\simeq120$ msec and, while $T_1$ is thus decreased by about 20 msec, $T_3$, $T_4$ and $T_5$ remain unchanged.

As apparent from this test, although the delay time $T_1$ varies considerably depending on the number of heart beats, it is necessarily less than the period of the heart beat. Accordingly, it is only necessary to be variable about within a range from 0 to 1000 msec, assuming the number of heart beat of a living body as from 60 to 200 cycles/min.

While on the other hand, since $T_3$, $T_4$, $T_5$ are attributable to the inherent movement of heart contraction and relaxation, these time periods are generally set to be variable within a range from 0 to 500 msec even in the case where the device is made utilizable in a general purpose, irrespective of the kind of animals.

The sucking or discharging volume $V_1$, $V_2$ ($V_1\simeq V_2$) is the amount related to the magnitude of the deviation between the abnormal blood flow waveform from the normal one. Since the blood flow rate is generally low in the case where the portion of the artery applied with the bypassing operation situates nearer to the periphery, $V_1$, $V_2$ may be relatively small, which is about 0.3 cm$^3$ in average for an adult dog and about 3 cm$^3$ in average for an adult person: it may be less than 10 cm$^3$ at the maximum even considering some allowance.

The variable adjusting range for the parameters $T_1$, $T_3$, $T_4$, $T_5$, $V_1$, $V_2$ may be broader than that as described above.

Figure 4:
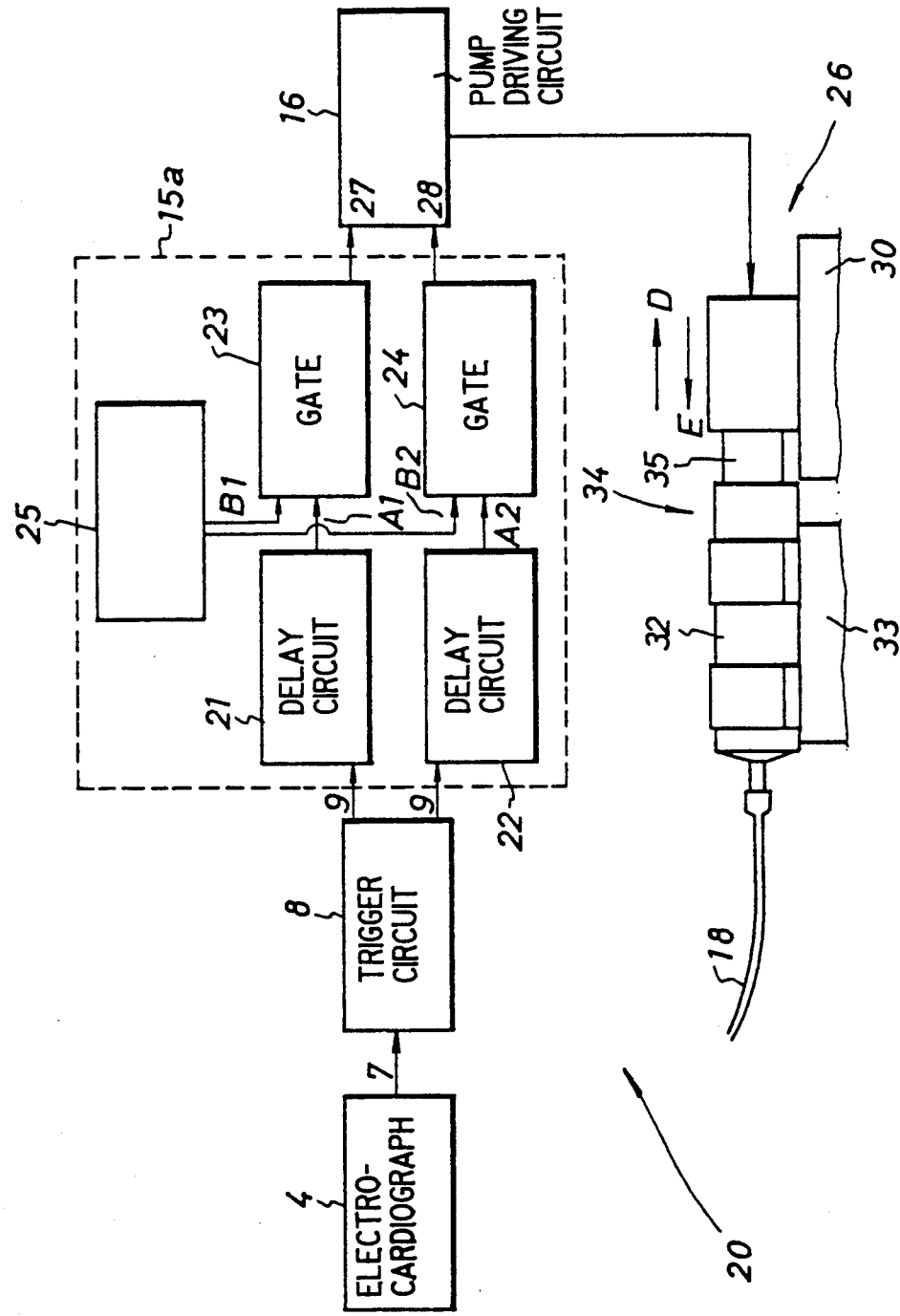
FIG. 4 is an explanatory view for a modified embodiment of the device in FIG. 3.

The medical pump device of a modified embodiment according to this invention will then be described referring to FIG. 4. Among the constituent elements of the device 20 in FIG. 4, the same elements as those in the device 19 in FIG. 3 carry the common reference numerals.

Figure 21:
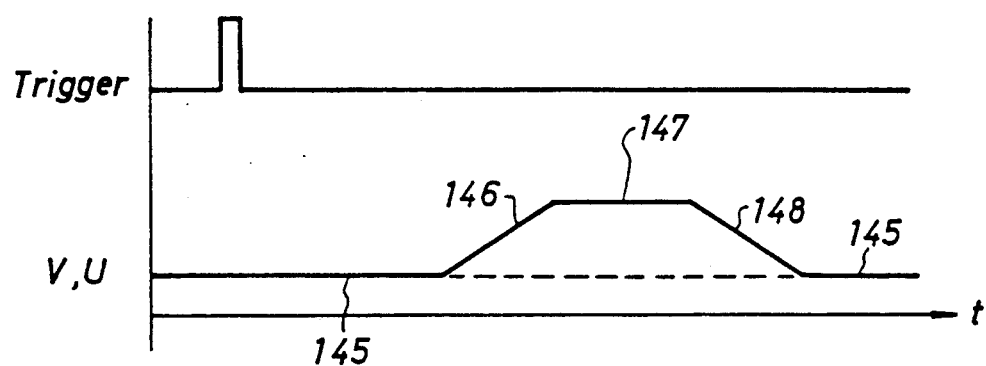

In FIGS. 4, 21 and 22 are delay circuits. Upon each reception of a trigger signal 9 from a trigger circuit 8 corresponding to the peak of the R wave in the pulsating signal 7 from the electrocardiograph 4, the two delay circuits 21, 22 generate such gate control signals $A_1$, $A_2$ as to open the gates 23 and 24 for the time periods $T_3$ ($=t_2-t_1$), and $T_5$ ($=t_4-t_3\simeq t_4-t_6$) of adjustable magnitude for the gates 23 and 24, from the time $t_1$ ($=t_0+T_1$) and $t_3$ or $t_6$ ($=t_0+T_2$) delayed each by the periods $T_1$ and $T_2$ ($=t_3-t_0$) of adjustable magnitude from the time $t_0$ at which these delay circuits 21 and 22 receive the signal 9.

25 is a pulse signal generator that generates pulse signals $B_1$ and $B_2$ at an adjustable predetermined pulse interval. The pulse signal $B_1$ applied to the gate 23 is supplied to the backward driving signal generating input 27 of the driving circuit 16, so as to provide a linear pulse motor 26 with a signal for backward (direction D) motion from the driving circuit 16 for a period $T_3$ from the time $t_1$ to $t_2$. Likewise, the pulse signal $B_2$ applied to the gate 24 is supplied to the forward driving signal generating input 28 of the driving circuit 16, so as to provide the linear pulse motor 26 with a signal for forward (direction E) motion from the driving circuit 16 for a period $T_5$ from the time $t_6$ to $t_4$. In this embodiment, the difference signal generator 15a comprises the delay circuits 21, 22, the gates 23, 24 and the pulse signal generator 25.

In the case where the catheter 18 is connected to the downstream side 3b to the reconstructed artery 3 as in FIG. 3, if the linear pulse motor 26 is driven backward, the linear pulse motor 26 moves on a motor rail stand 30 in the direction D. By this move, the inner cylinder or inner plunger 35 of an injection cylinder-like pump 34 whose outer cylinder or hollow cylinder 32 is secured to a support bed 33 is also displaced in the direction D relative to the hollow cylinder portion 32. Accordingly, blood is sucked into the catheter 18 from the downstream region 3b of the reconstructed artery 3.

While on the other hand, if the linear pulse motor 26 is driven forward, the linear pulse motor 26 moves in the direction E. By this movement, the plunger portion 35 integral therewith is displaced in the direction E and the blood is returned from the catheter 18 to the downstream region 3b of the reconstructed artery 3.

In the case of the device 20, $V_1$ and $V_2$ can be adjusted by varying the frequency of the pulse from the pulse generator 25 or the diameter of the injection cylinder 34.

While the forward and backward movements are obtained directly from the linear pulse motor in the device as described above, a system of obtaining forward and backward movements by the combination of ordinary rotary type pulse motor and lead screw may be employed, instead.

Figure 5:
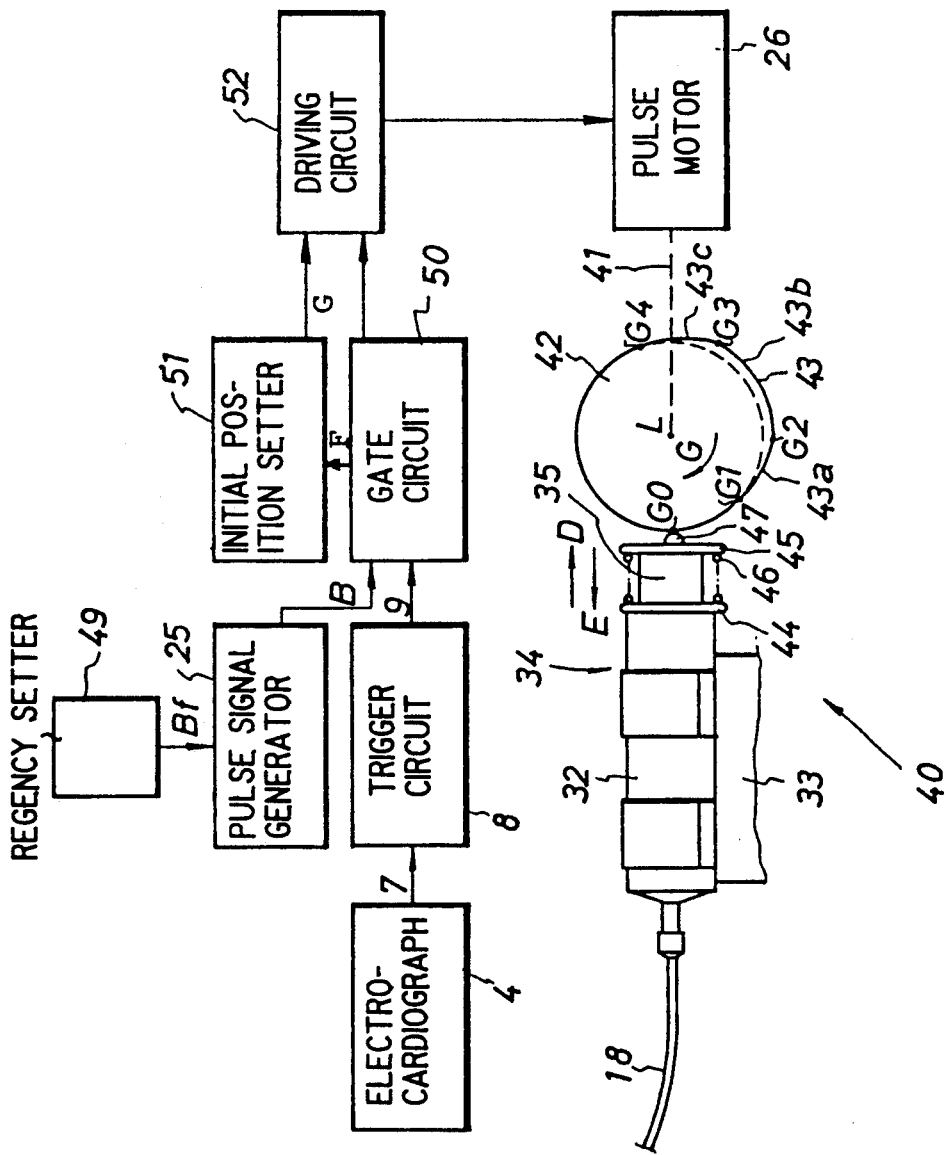
FIG. 5 is an explanatory view for another modified embodiment of the device in FIG. 3.

FIG. 5 shows a medical pump device 40 as a further modified embodiment. In the pump device 40 of FIG. 5, the same elements as those in the pump device 19 or 20 in FIGS. 3 or 4 carry the common reference numerals.

Figure 6:
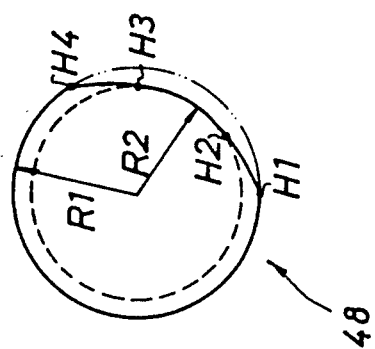
FIG. 6 is an explanatory view for a modified embodiment of a cam plate of the device in FIG. 5.

In the pump device 40 of FIG. 5, the control for the movement of the inner cylinder 35 in the direction D or E relative to the outer cylinder 32 is performed by urging a cam follower protrusion 47 of an end flange 45 of the inner cylinder 35 to the cam face 43 of a cam plate 42, connected to a power shaft 41 of the pulse motor 26, by means of a compression spring 46 between the flanges 44 and 45. In this cam device, when the cam plate 42 rotates in the direction G, the inner cylinder 35 is urged to displace in the direction E while the cam face 43a between the positions $G_1$ and $G_2$ is in contact with the protrusion 47, the displacement of the inner cylinder 35 in the direction E is interrupted while the cam face 43b with a constant diameter between the positions $G_2$ and $G_3$ is in contact with the protrusion 47, and the inner cylinder 35 is returned in the direction D by the extending force of the spring 46 while the cam face 43c between the positions $G_3$ and $G_4$ is in contact with the protrusion 47. The cam plate 42 is used in the case of connecting the catheter 18 to the upstream side 3c of the reconstructed artery 3. In the case of connecting the catheter 18 to the downstream side 3b of the reconstructed artery 3, a cam plate 48 as shown in FIG. 6 having a constant diameter $R_1$ between the positions $H_4$ and $H_1$, a constant diameter $R_2$ ($<R_1$) between the positions $H_2$ and $H_3$ and a diameter monotonously changing between the positions $H_1$ and $H_2$ and positions $H_3$ and $H_4$, respectively, may be used in place of the cam plate 42.

In the pump device 40, 49 is a frequency setter for setting the generation frequency $B_f$ for the pulse B from the pulse generator 25, and 50 is a gate circuit for allowing the passage of the pulse signal B at the frequency $B_f$ for a predetermined time $T_a$ (($t_5-t_0$)$<T_a<T_0$) on every application of a trigger signal 9 from the trigger circuit 8. 51 is an initial position setter for setting the initial position $G_0$ for the cam plate 42 and it delivers an initial position signal G to the driving circuit 52 upon receiving the operation end signal F from the gate circuit 50, by the operation end signal F.

52 is a driving circuit for the step motor 26, and the driving circuit 52 sets the cam plate 42 to a position where the position $G_0$ defined by the setter 51 is abutted against the protrusion 47. When a signal showing the peak of the R wave is given from the electrocardiograph 4 at the time $t_0$, the trigger circuit 8 is actuated and the pulse signal B at the frequency $B_f$ is applied to the driving circuit 52 passing through the gate circuit 50 for a period $T_a$ thereafter. Accordingly, the driving circuit 52 rotationally drives the cam 42 by way of the pulse motor 26 in the direction G at a speed defined with the frequency $B_f$ to control the movement of the inner cylinder 35 in the direction D, E and performs the discharge and sucking of the liquid to and from the vicinity 3a of the reconstructed artery by way of the catheter 18. The cam plate 42 is set again to the initial position $G_0$ under the control of the circuits 51, 52 after an elapse of the period $T_a$ and before the delivery of the next signal 7.

In the pump device 40, the difference signal generator 15a comprises the pulse generator 25, the gate circuit 50, and the initial position setter 51.

In the pump device 40, if the pulse frequency $B_f$ is constant, the time periods $T_1$, $T_3$, $T_4$ and $T_5$ are defined with angle $G_0LG_1$, angle $G_1LG_2$, angle $G_2LG_3$ and angle $G_3LG_4$, respectively, while $V_1$ and $V_2$ are defined with the shape of the cam face 43a from $G_1$ to $G_2$ and the cam face 43c from $G_3$ to $G_4$, respectively, as well as the inner diameter of the injection cylinder-like pump 34. L represents a cam rotating center.

Figure 7:
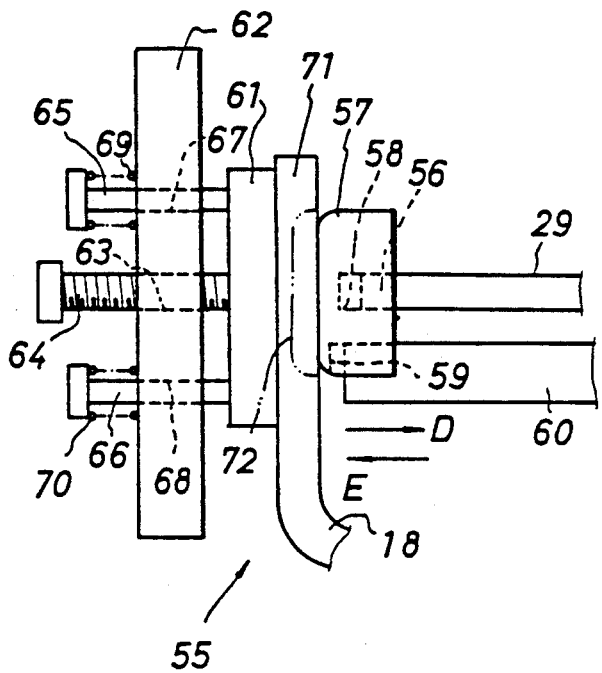
FIG. 7 is an explanatory view for a modified embodiment of a portion of the device in FIG. 5.

In the pump device 20 of FIG. 4, a pump 55 as shown in FIG. 7 may be used in place of the injection cylinder-like pump 34. In the pump 55 of FIG. 7, the top end 56 of a connection rod 29 connected to a motor head is joined into the aperture 58 of a pinch member 57. The pinch member 57 is engaged at a recess 59 thereof with a guide member 60 such that it is displaced in the direction D by the backward movement of the motor 26 and in the direction E by the forward movement of the motor 26.

61 is a support bed and its position in the direction D or E is adjusted by a stand position adjusting screw 64 screw-coupled to the threaded hole 63 in a frame 62. 65 and 66 are guide rods secured to the support bed 61 and the guide rods 65 and 66 penetrate guide holes 67 and 68, respectively, in the frame 62. 69 and 70 are compression springs. In the pump 55, when the pinch member 57 is displaced in the direction E or D by the forward or backward movement of the connection rod 29 connected to the motor head of the motor 26, after setting the support bed 61 to a predetermined position by the screw 64, the displaced state as shown by the dotted chain (phantom line) at the portion 72 of a flexible tube 18 closed at one end 71 is changed, by which the inner volume of the tube 18 is changed to perform the discharge or sucking of the liquid. The flow rate $V_1$, $V_2$ can be adjusted by varying the stroke in the direction D, E or the urging area. The tube 18 may be the catheter itself or a separate member in communication with the catheter 18, which can be made of a flexible baloon for instance.

Figure 8:
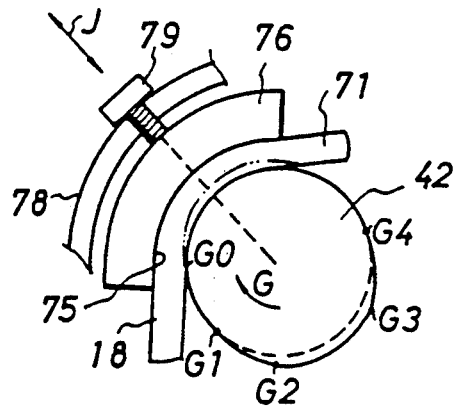
FIG. 8 is an explanatory view for a modified embodiment of a portion of the device in FIG. 5.

In the case of using the pump of a system urging to deform the flexible tube 18 as shown in FIG. 7 instead of the injection cylinder-like pump 34 in FIG. 4, a plurality of them may be connected in parallel or in series as required to control the flow rate or the introduction timing. Further, the cam 42 in FIG. 5 may be combined with a support bed 76 having an arcuate supporting face 75 as shown in FIG. 8 to constitute a pump 77 utilizing the deformation of the tube 18. Further, the position of the supporting bed 76 in the radial direction J is adjusted by a screw 79 screw-coupled into a frame 78.

Figure 9:
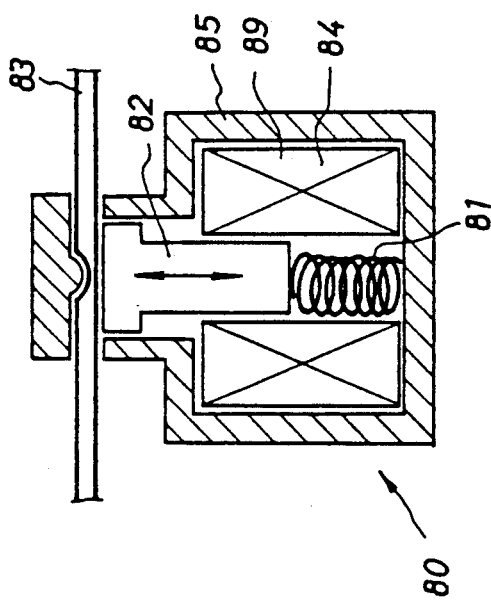
FIGS. 9 through 14 are explanatory views for modified embodiments of the device according to this invention.

Then, a device by an electromotive solenoid driving will now be explained as a further modified embodiment referring to FIGS. 9 through 14. A solenoid pinch valve 80 has a structure as shown in FIG. 9, in which a plunger 82 is urged upward by a spring 81 upon non-energized, state and a tube 83 put between the plunger 82 and a casing 85 is crushed (pinched ). When the solenoid 89 is energized, the plunger 82 is attracted by the force of an electromagnet 84 to release the tube 83. Since the inner volume of the tube 83 varies by a constant amount depending on the pinching and releasing operation, the liquid in the tube 83 also moves left and rightward. When a silicon tube 83 of 3 mm in inner diameter (5 mm in outer diameter) is opened and closed with a pinching width of about 5 mm, the volume movement was about 0.1-0.08 cc. For the valve 80, a solenoid pinch valve of a function closing the tube 83 upon activation (excitation) of the electromagnet 84, and opening the tube 83 upon deactivation may be used.

Figure 10:
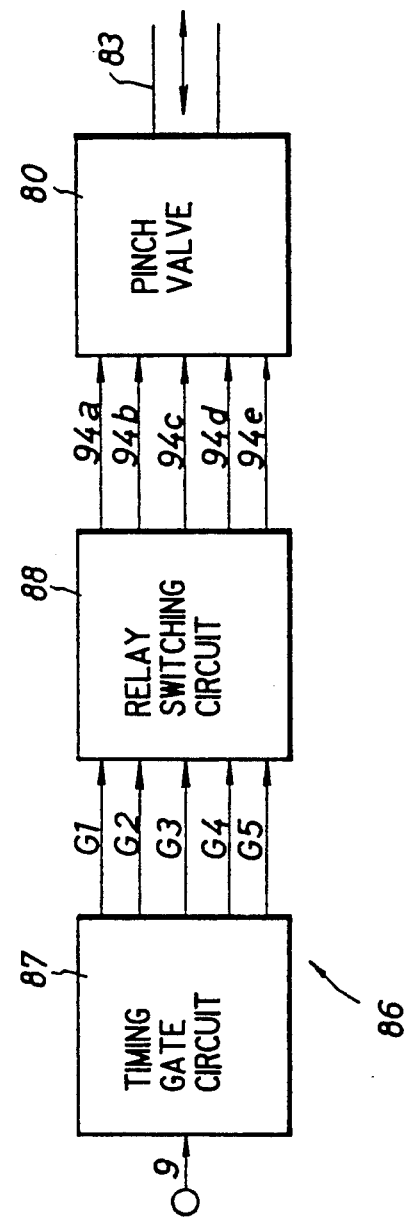

The outline of the liquid pump device 86 applied with this operation mechanism is shown in FIG. 10. A timing gate circuit 87 receives a synchronization input signal 9 from an electrocardiograph, etc and generates gate pulse signals with a time width $nD_1+D_2+nD_3$ (n is an integer) after a certain time delay $D_0+mD_1$ (m is an integer) from the time at which the gate circuit 87 has received the input signal 9. A relay switching circuit 88 receives the gate signals as described above to open and close a power relay. The relay circuit controls the electromagnetic opening and closure of the pinch valve 80 at the final stage. In this device 86, it is attempted to constitute such that five solenoid pinch valves 80a, 80b, 80c, 80d and 80e are opened or closed successively by the relay circuit 88 so as to perform smooth charge or discharge of the liquid in an appropriate amount, considering that the charge or discharge liquid amount per one valve is small ($\lesssim 0.1$ cc) and that adjustment for the operation speed of the solenoid 89 is impossible to provide an instantaneous discharge or sucking operation.

Figure 11:
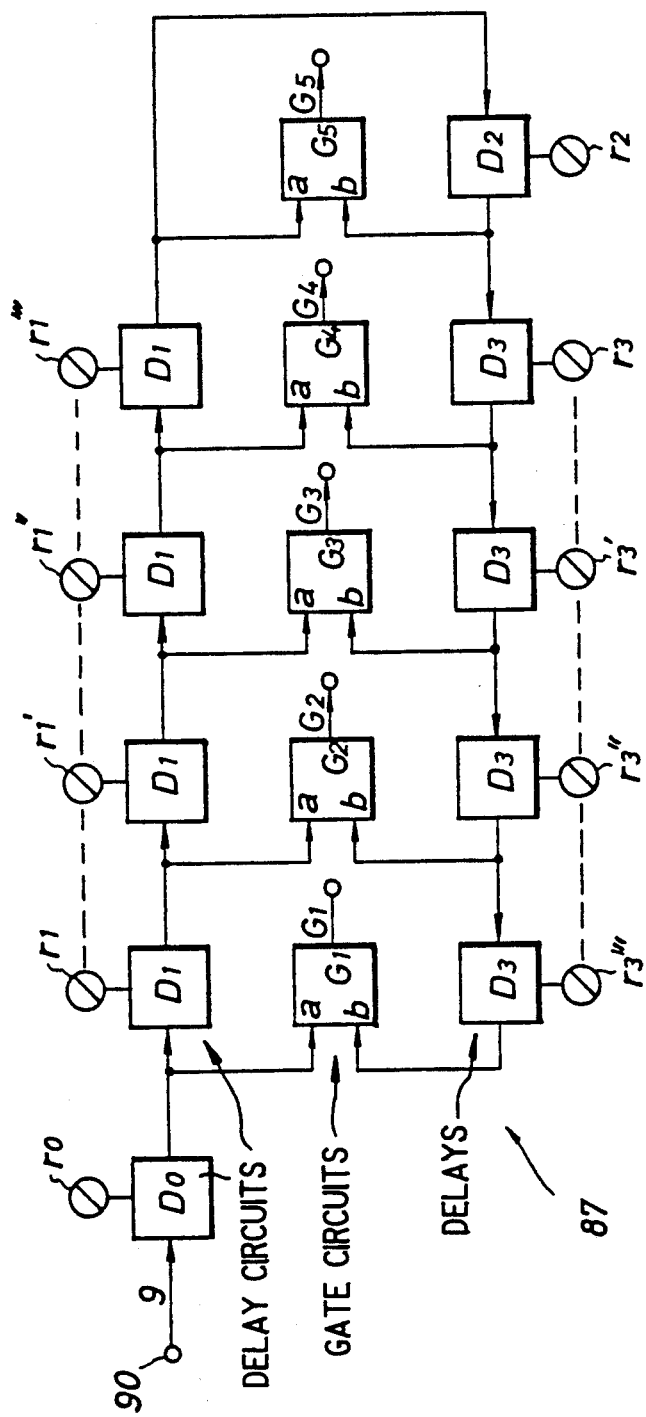
Figure 12:
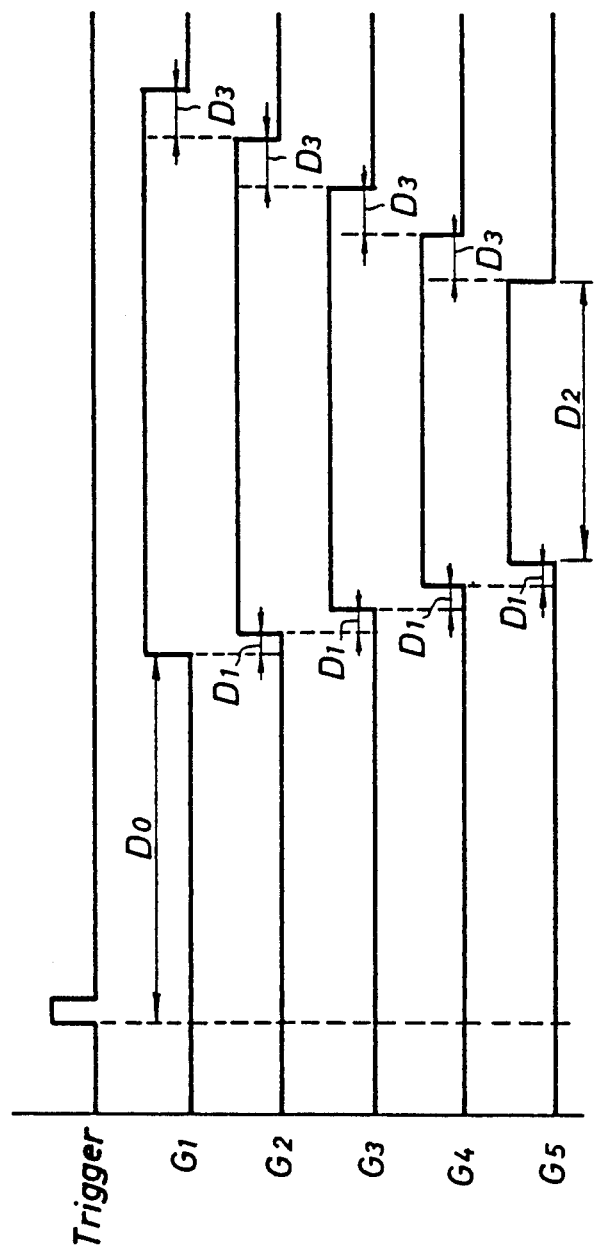
Figure 13:
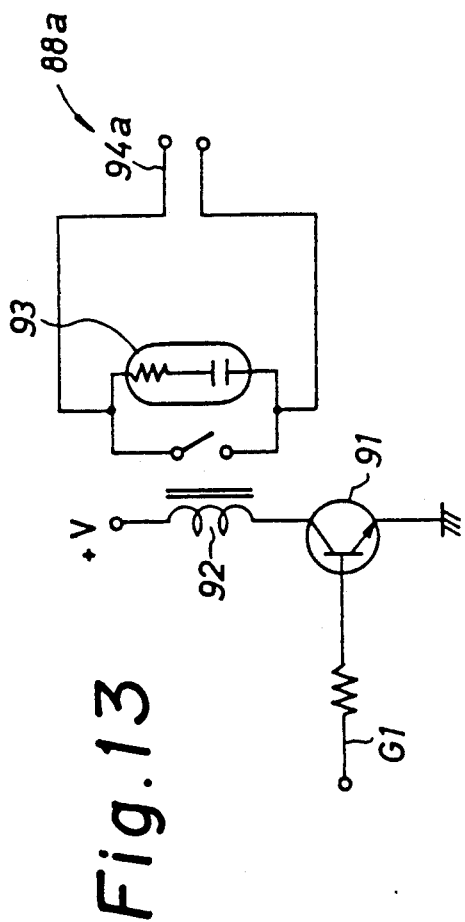

The timing gate circuit 87 has a constitution as shown in FIG. 11. It comprises an input terminal 90 for a trigger signal 9; delay circuits $D_0$, $D_1$, $D_2$ and $D_3$, which generate timing trigger signals successively from the input time of the trigger signal 9 with appropriate time delays; and gate circuits $G_1$-$G_5$ supplied with these timing trigger signals at inputs a, b as the gate ON or OFF signal to generate gate pulses $G_1$-$G_5$ at a TTL level "1 (high)" only for the predetermined time width (from the ON trigger input time to the OFF trigger input time) from a predetermined time. These delay times (or time width) can variably be set by adjusters $r_0$, $r_1$-$r_1'''$, $r_2$, $r_3$-$r_3'''$. $r_1$-$r_1'''$ operate interlockingly and $r_3$-$r_3'''$ also operate interlockingly. The relationship between the gate signals $G_1$-$G_5$ finally outputted from the circuit 87 and the trigger input pulse is shown in FIG. 12. $G_1=$"1" after the time $D_0$ from the rising time of the trigger input signal 9 and, thereafter, the gate signals $G_2$-$G_5$ attain "1" with the time delay $D_1$ successively. $G_5$ goes "0 (low)" after the time $D_2$. From the time of $G_5=$"1" and, thereafter, the gate signals $G_4$-$G_1$ return to the state "0" with the successive time delay $D_3$. These gate signals control a relay switching circuit 88 at the succeeding stage. The relay switching circuit 88 comprises five circuits 88a, 88b, 88c, 88d, 88e disposed in parallel to each other corresponding to the signals $G_1$-$G_5$ and an example of the circuit 88a is shown in FIG. 13. A transistor 91 turns to ON or OFF state in accordance with the TTL gate signals $G_1$-$G_5$ to open or close a relay 92 connected therewith. Instead of this circuit, a TTL-driven solid state relay (SSR), etc may be used. 93 is a surge absorber and 94a is an output of the relay switching circuit 88a.

Figure 14:
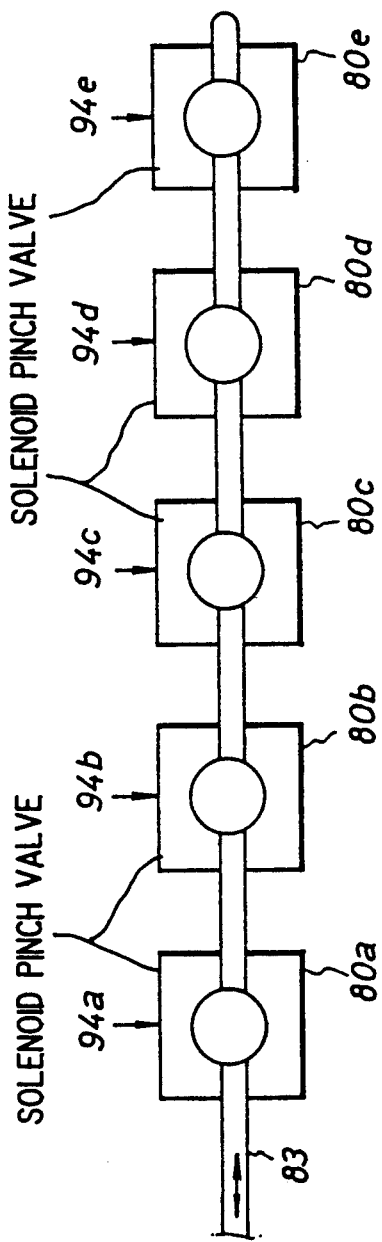

The five solenoid pinch valves 80a-80e are arranged as shown in FIG. 14 and opened in the order of 80a-80b-80c-80d-80e, while closed in the order of 80e-80d-80c-80b-80a, the timing shown previously in accordance with the on-off mode driving voltage 94a,-94e from the relay circuits 88a-88e, to suck or discharge the liquid in the tube 83 connected therewith successively and closed at one end thereof. In the case where the sequence of the sucking and discharge is intended to be reversed, the gate signal connection is reversed (connecting the signal 94a to the valve 80e,-94e to the valve 80a) and the gate output signal is reversed. Alternatively, a solenoid pinch valve which is opened in the deenergization state, while closed upon energization may be used. In the case of adjusting the open time delay as: $D_1=0$ and the closed time delay as: $D_3=10$ msec with this device 86, a performance suitable to the sufficient practical use with the sucking time up to 50 msec, discharge time up to 50 msec and moving volume of about 0.4 cc could be attained. Although this device 86 is adapted as a serial liquid charge and discharge type, it may be operated while connecting the five tubes in parallel depending on the opening and closing times. Further, the variation for the moving volume can simply be attained by changing the tube diameter.

Figure 15:
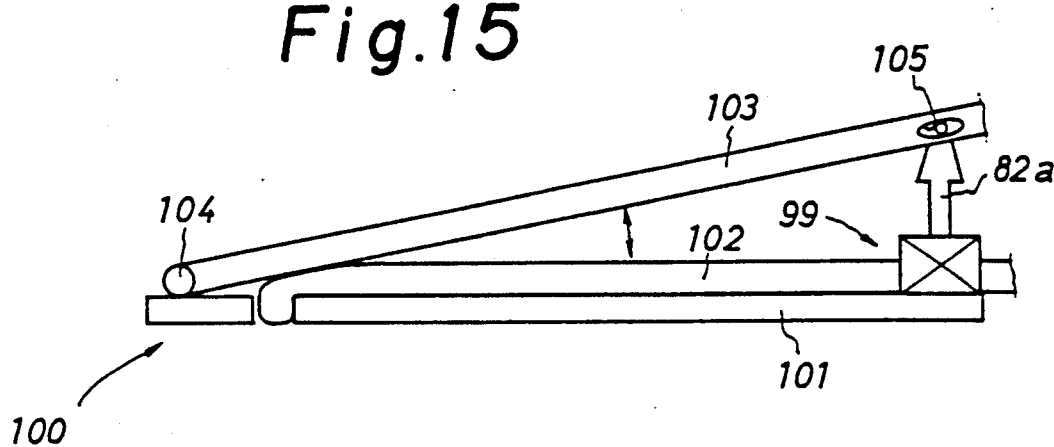
FIG. 15 is an explanatory view for another modified embodiment.

Although the smooth liquid charge and discharge are performed by interlocking the five solenoid pinch valves 80 in the device 86 described above, smooth discharge can also be attained by one solenoid device 99 by selecting a device 100 as shown in FIG. 15. A tube 102 to be urged is secured on a securing table 101 and a pinch arm 103 is secured at the left end thereof with a rotating fulcrum 104 while connected at the other end to the plunger 82a of a solenoid 99 at a position 105, in which the tube 102 is closed at the left end thereof. When the solenoid 99 actuates so as to attract downward the plunger 82a, the pinch arm 103 is pulled to successively urge the tube 102 from the left end and thereby discharge the liquid from the tube 102. When the solenoid 99 performs the opening operation, the diameter of the tube 102 is restored by the opposite operation to suck the liquid.

Figure 16:
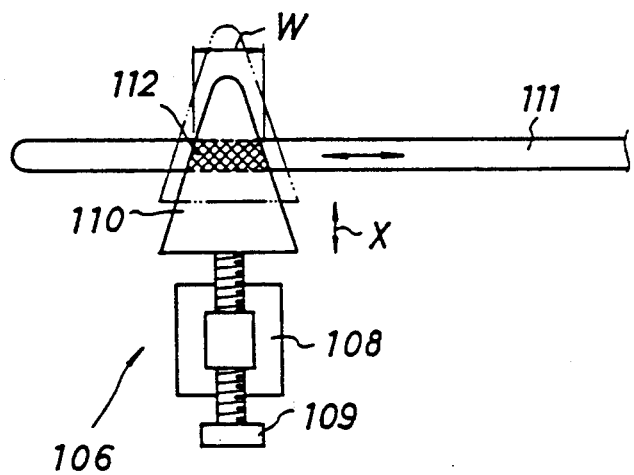
FIG. 16 is an explanatory view for a further modified embodiment.
Figure 17:
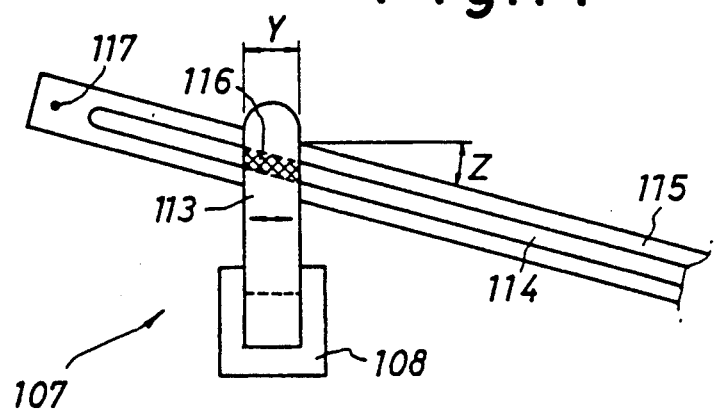
FIG. 17 is an explanatory view for a still further modified embodiment.

Devices 106 and 107, capable of variably adjusting the liquid charge and discharge amount continuously and finely, are shown in FIGS. 16 and 17, respectively. In FIG. 16, a pinch plate 110 which is formed into a shape of an acute-angle and secured to a solenoid plunger 108 by means of a moving screw 109 is used. In this figure, the solenoid plunger 108 moves vertically (in the direction vertical to the sheet of FIG. 16) and urges a tube 111 secured to a table (not shown) by a certain width W formed by contact of the pinch plate 110 with the tube 111 which is closed at one end thereof. The pinch width W can be adjusted by moving the moving screw 109 thereby moving the pinch plate 110 in the direction X. The region 112 depicted by the hatched lines is a pinch region. In FIG. 17, the magnitude or the pinch area of a pinch region 116 is made variable thereby adjusting the charge and discharge amount by varying an angle Z of a securing table 115 for the tube 114 relative to a pinch plate 113 having a predetermined width Y. The tube 114 is disclosed at one end thereof. 117 is a fulcrum.

Figure 18:
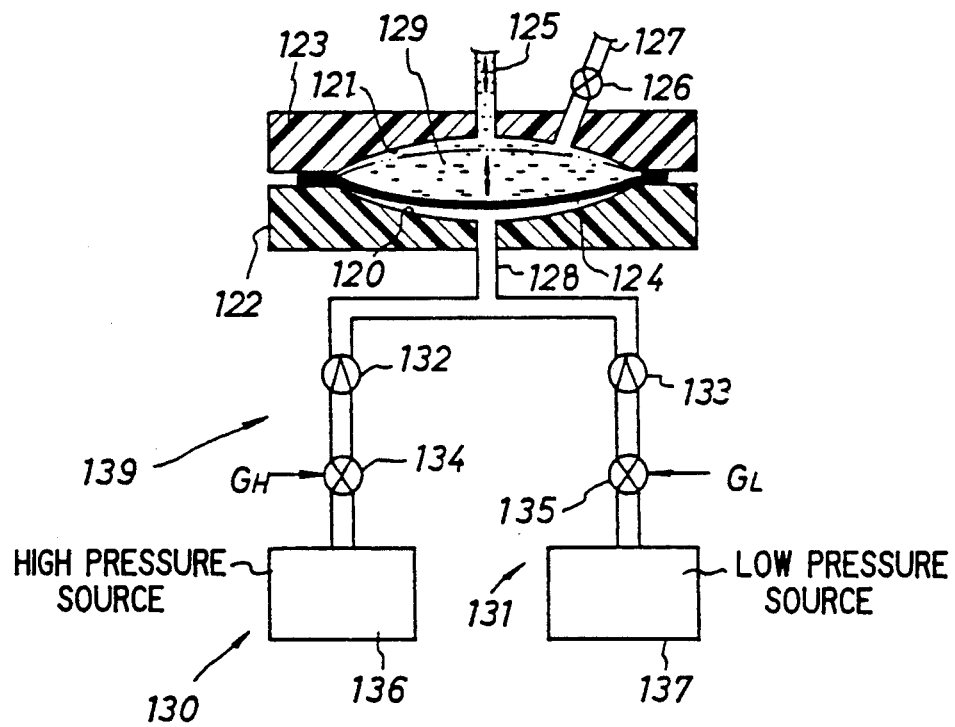
FIGS. 18 and 19 are explanatory views for yet further modified embodiments and FIGS. 20 and 21 are explanatory views for still further embodiments.
Figure 19:
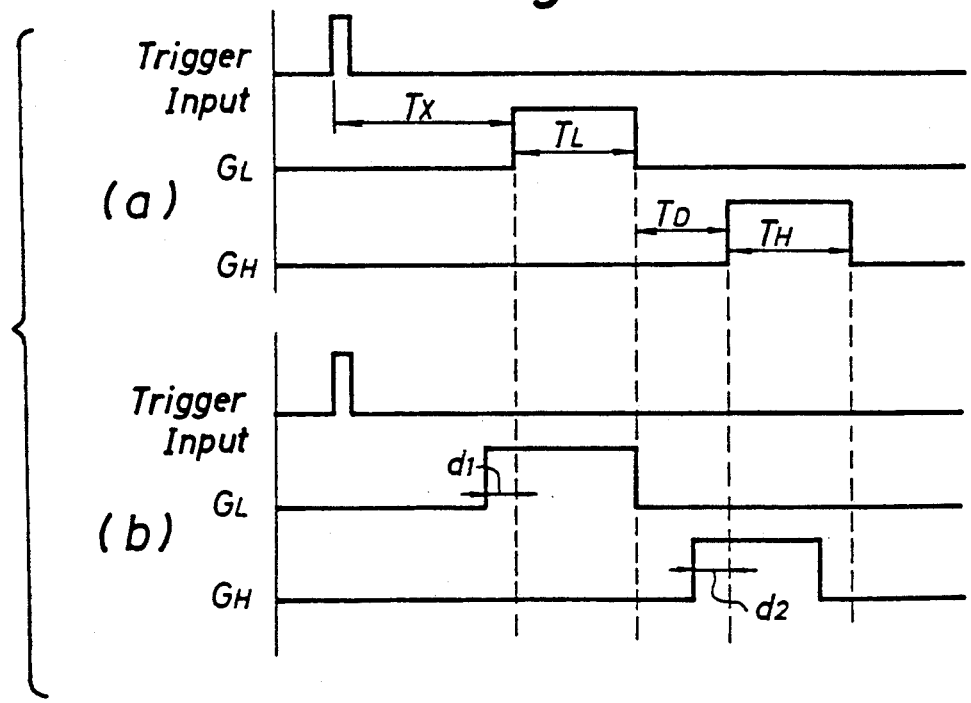

A device 139 for a further modified embodiment is shown in FIG. 18. Circular members 122, 123, made of an acrylic or "Teflon" resin, with recessed faces 120, 121, respectively, at the middle portion thereof are prepared. A flexible thin sheet 124 of silicon rubber or the like is put therebetween to constitute a diaphragm as shown in the drawing. A liquid charge or discharge tube 125 and a vent 127 with a valve 126 are attached to the upper vessel 123, while a tube 128 for diaphragm actuating fluid is attached to the lower vessel 122. Liquid to be delivered or sucked is filled on the upper side of the diaphragm sheet 124. The tube 128 coming out of the lower vessel 122 is divided into two systems and connected to delivering and sucking devices 130 and 131. They are respectively connected to a high pressure source 136 and a low pressure source 137 for hydraulic fluid by way of flow rate control valves 132 and 133 and operation controlling solenoid valves 134 and 135 which are opened or closed by electrical signals, respectively. While air, oil, etc are used as the hydraulic fluid, since air may cause a delay in response due to its compressible nature, oil pressure is desirable for the high speed operation. The relationship between two signals $G_H$ and $G_L$ for the solenoid valves 134 and 135 together with the trigger input signal are shown in FIG. 19, graphs (a), (b). In the case where it is intended to perform sucking for $T_L$, stopping for $T_D$ and discharging for $T_H$ after the time $T_X$, a control signal as shown in FIG. 19, graph (a), may be used, assuming that there is no operation delay and the response is quick as in the oil pressure system. Delay times $d_1$ and $d_2$ are disposed as shown in FIG. 19, graph (b), where there is a response delay as in the pneumatic pressure system.

Figure 20:
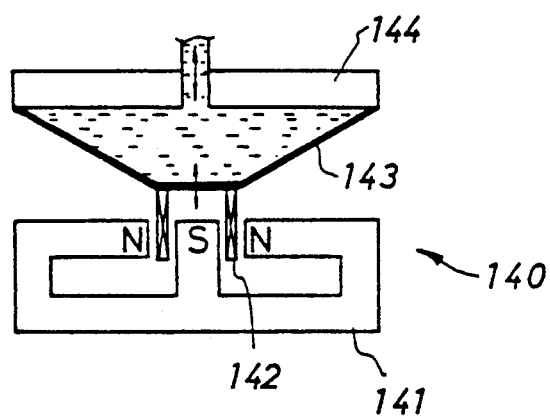

FIGS. 20 and 21 shown a still further modified embodiment. This device 140 of a coreless or cored dynamoelectric driven electromagnet type, like a loud speaker, utilizes the phenomenon that the moving electromagnet 142 moves by supplying an electrical current into the electromagnet 142 placed in the magnetic field of a permanent magnet 141. The upper end of the moving electromagnet 142 is secured to the center of a diaphragm 143 made of a flexible membrane such as silicon rubber. The diaphragm 143 is moved along with the displacement of the moving electromagnet 142, by which the liquid between the diaphragm 143 and the flange 144 moves. Since the position V (displacement) for the moving electromagnet 142 corresponds to the electromagnet current U, the operation for sucking, stopping and delivery can be performed by controlling the electrical current U flowing through the moving electromagnet 142 as shown in FIG. 21. 145 corresponds to the initial displacement (position), 146 to the sucking (or delivering) operation, 147 to the final displacement (position) and 148 to the delivering (or sucking) operation.

I claim:

1. A medical pump apparatus for compensating a deviation of a measured blood flow rate in an artery from a reference blood flow rate to thereby bring said measured blood flow rate near to said reference blood flow rate, comprising:

means for detecting a heart beat and outputting a triggering signal in response to said detected heart beat;

means for measuring a blood flow rate in said artery and for outputting a measured blood flow rate signal;

memory means for storing a reference blood flow rate signal;

means for determining a first difference and a second difference in response to said reference blood flow rate signal from said memory means and said measured blood flow rate signal from said blood flow rate measuring means to thereby issue a characterizing signal representing said first and second differences in response to said triggering signal from said heart beat detecting means, said first difference comprising a difference between said reference blood flow rate and said measured blood flow rate during a first period in which said measured blood flow rate is less than said reference blood flow rate, said second difference comprising a difference between said reference blood flow rate and said measured blood flow rate during a second period in which said measured blood flow rate is more than said reference blood flow rate;

means for discharging a liquid from a source of said liquid to said artery and for sucking said discharged liquid from said artery in response to said characterizing signal; and means for connecting said discharging and sucking means to said artery.

2. A medical pump apparatus according to claim 1, in which said heart beat detecting means comprises an electrocardiograph connectable to a patient for detecting said heart beat to thereby issue a heart beat signal, and a trigger circuit for issuing said triggering signal in response to the heart beat signal from said electrocardiograph.

3. A medical pump apparatus according to claim 1, in which said discharging and sucking means comprises a single port through which the liquid is discharged to and sucked from said artery.

4. A medical pump apparatus according to claim 3, in which said discharging and sucking means comprises a flexible tube closed at one end thereof, and solenoid pinch valves, said flexible tube is disposed between a plunger of each of said solenoid pinch valves and a casing of each of said solenoid pinch valves, said flexible tube being pinched by the solenoid pinch valves so that a liquid received therein is sequentially discharged and sucked.

5. A medical pump apparatus according to claim 3, in which said discharging and sucking means comprises a linear pulse motor and a drive circuit electrically connected to said linear pulse motor.

6. A medical pump apparatus according to claim 3, in which said discharging and sucking means comprises syringing means driven by a rotary cam plate connected to a power shaft of said linear pulse motor.

7. A medical pump apparatus according to claim 1, in which said blood flow rate measuring means comprises means for displaying said measured blood flow rate as a function of time.

8. A medical pump apparatus according to claim 1, in which said blood flow rate measuring means is a blood flow meter.

9. A medical pump apparatus according to claim 1, in which said blood flow rate measuring means is adapted to measure said blood flow rate to issue said measured blood flow rate signal simultaneously with an operation of said discharging and sucking means, and said first and second difference determining means is adapted to determine, simultaneously with said operation, said first and second differences in response to said stored reference blood flow rate signal from said memory means and said simultaneously measured blood flow rate signal from said blood flow rate measuring means to thereby issue said characterizing signal to said discharging and sucking means in response to said triggering signal from said heart beat detecting means.

10. A medical pump apparatus according to claim 1, in which said blood flow rate measuring means is adapted to measure said blood flow rate to issue said measured blood flow rate signal previously to an operation of said discharging and sucking means, and said first and second difference determining means is adapted to determine said first and second differences in response to said stored reference blood flow rate signal from said memory means and said previously measured blood flow rate signal from said blood flow rate measuring means to thereby issue said characterizing signal to said discharging and sucking means in response to said triggering signal from said heart beat detecting means.

11. A method for compensating a deviation of a measured blood flow rate in an artery from a reference blood flow rate to thereby bring said measured blood flow rate near to said reference blood flow rate, comprising the steps of:
  detecting a heart beat and outputting a triggering signal in response to said detected heart beat;
  measuring a blood flow rate in said artery and outputting a measured blood flow rate signal;
  storing a reference blood flow rate signal;
  determining a first difference and a second difference in response to said reference blood flow rate signal said and said measured blood flow rate signal to thereby issue a characterizing signal representing said first and second differences in response to said triggering signal,
  said first difference comprising a difference between said reference blood flow rate and said measured blood flow rate during a first period in which said measured blood flow rate is less than said reference blood flow rate,
  said second difference comprising a difference between said reference blood flow rate and said measured blood flow rate during a second period in which said measured blood flow rate is more than said reference blood flow rate; and
  discharging a liquid to said artery sucking said discharged liquid from said artery in response to said characterizing signal.

12. A method according to claim 11, which comprises the steps of discharging said liquid to said artery based on said first difference and sucking said liquid from said artery based on said second difference.

13. A method according to claim 11, which comprises the steps of discharging said liquid to said artery based on said second difference and sucking said liquid from said artery based on said first difference.

14. A method according to claim 11, which comprises the steps of measuring a blood flow rate in said artery to thereby display said measured blood flow rate as a function of time.

15. A method according to claim 11, in which said steps of measuring said blood flow rate and of determining said first and second differences are carried out simultaneously with said step of discharging said liquid to said artery and sucking said discharged liquid from said artery.

16. A method according to claim 11, in which said steps of measuring said blood flow rate and of determining said first and second differences are carried out previous to said step of discharging said liquid to said artery and sucking said discharge liquid from said artery.

* * * * *

UNITED STATES PATENT AND TRADEMARK OFFICE
CERTIFICATE OF CORRECTION

PATENT NO. : 5,006,111
DATED : April 9, 1991
INVENTOR(S) : Inokuchi et al

It is certified that error appears in the above-identified patent and that said Letters Patent is hereby corrected as shown below:

Column, 1, line 11, change "intention" to --invention--;
line 21, change "the referenced blood" to --the reference blood--.

Column 4, line 44, change "D to thereby" to --D, to thereby--.

Column 5, lines 34 and 35, change "approximating $t_o$" to --approximating to--;
line 45, change "patterns" to --pattern--;
line 46, change "$K_2,+K_3$" to --$K_2+K_3$--;
line 50, change "$t_1$" to --$t_1-t_3$--;
line 55, change "that is" to --(that is--;
line 56, change "$t_3=t_2-t_1$" to --$T_3=t_2-t_1$--;
line 57, change "$T_5=t_4-T_3$" to --$T_5=t_4-t_3$)--;
line 59, change "that are made" to --that is, are made--.

Column 6, line 51, change "delayed" to --which are delayed--.

Column 8, line 5, delete ", by the operation end signal F";
lines 25 and 26, change "difference signal generator 15a" to --comparator 15--.

UNITED STATES PATENT AND TRADEMARK OFFICE
CERTIFICATE OF CORRECTION

PATENT NO. : 5,006,111

DATED : April 9, 1991

INVENTOR(S) : Inokuchi et al

It is certified that error appears in the above-identified patent and that said Letters Patent is hereby corrected as shown below:

Column 9, lines 14 and 15, change "non-energized, state" to --non-energized state--;
 line 68, change "the time $D_2$. From" to --the time period $D_2$ from--.

Column 10, line 17, change "the timing" to --with the timing--.

Column 11, line 7, change "disclosed at one" to --closed at one--;
 line 43, change "FIGS. 20 and 21 shown" to --FIGS. 20 and 21 show--.

Column 14:

Claim 11, line 13, delete "said" (first occurrence).
 line 27, insert --and-- after "artery".

UNITED STATES PATENT AND TRADEMARK OFFICE
CERTIFICATE OF CORRECTION

PATENT NO. : 5,006,111

DATED : April 9, 1991

INVENTOR(S) : Inokuchi et al.

It is certified that error appears in the above-identified patent and that said Letters Patent is hereby corrected as shown below:

Claim 16, line 5, change "discharge" to --discharged--.

Signed and Sealed this

Second Day of February, 1993

Attest:

STEPHEN G. KUNIN

*Attesting Officer*  Acting Commissioner of Patents and Trademarks